United States Patent [19]
Dygos et al.

[11] Patent Number: 5,432,284
[45] Date of Patent: Jul. 11, 1995

[54] PROCESS FOR THE PREPARATION OF HETEROCYCLIC ALKYLAMIDE DERIVATIVES

[75] Inventors: John H. Dygos, Northbrook; Thomas R. Kowar, Mt. Prospect; Kathleen T. McLaughlin, Arlington Heights; Gatis Plume, Buffalo Grove; Michael L. Prunier, Vernon Hills; Richard J. Salzmann, Chicago; Mike G. Scaros, Arlington Heights; Joseph J. Wieczorek, Cary, all of Ill.

[73] Assignee: G. D. Searle & Co., Chicago, Ill.

[21] Appl. No.: 118,073

[22] Filed: Sep. 8, 1993

[51] Int. Cl.$^6$ .............. C07D 207/09; C07D 211/32; C07D 211/60
[52] U.S. Cl. .................... 546/230; 546/233; 546/234; 548/567; 548/508
[58] Field of Search .............. 546/233, 234, 230; 564/409, 396; 548/567, 568

[56] References Cited

U.S. PATENT DOCUMENTS

| | | | |
|---|---|---|---|
| 3,067,253 | 12/1962 | Dietzler et al. | 260/575 |
| 3,073,865 | 1/1963 | Spiegler | 260/580 |
| 3,145,231 | 8/1964 | Kosak | 260/580 |
| 3,148,217 | 9/1964 | Freyermuth et al. | 260/580 |
| 3,158,646 | 11/1964 | Dorfman et al. | 260/501 |

(List continue on next page.)

FOREIGN PATENT DOCUMENTS

| | | |
|---|---|---|
| 0343307 | 11/1989 | European Pat. Off. |
| 1191610 | 5/1970 | United Kingdom . |
| 1440991 | 6/1976 | United Kingdom . |
| 1483330 | 8/1977 | United Kingdom . |
| 1498722 | 1/1978 | United Kingdom . |

OTHER PUBLICATIONS

Hartung & Simonoff, Organic Reactions, 7, pp. 263 to 326 (1953), John Wiley & Sons, Inc.
Paul N. Rylander, Hydrogenation Methods, (1985), pp. 148, 163 to 164, Academic Press.
Morris Freifelder, Practical Catalytic Hydrogenation, (1971), pp. 413, 446–447, Wiley-Interscience.

(List continue on next page.)

Primary Examiner—C. Warren Ivy
Assistant Examiner—Raymond Covington
Attorney, Agent, or Firm—Joy A. Serauskas; Roger A. Williams

[57] ABSTRACT

The present invention relates to a novel process for the preparation of heterocyclic alkylamide derivatives having the following formula:

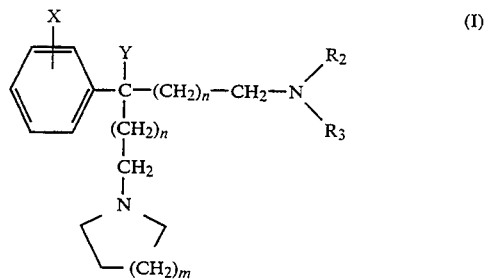

and the pharmaceutically acceptable acid addition salt thereof wherein X represents halo, alkyl having 1 to 6 carbon atoms, hydrido, trifluoromethyl, phenyl, or lower alkoxy having 1 to 6 carbon atoms; Y represents the group —CN or —CONH$_2$; R$_2$ represents alkyl having 1 to 6 carbon atoms; R$_3$ represents acetyl, benzoyl, phenacetyl or trifluoroacetyl; m is the integer 1 or 2 and n is an integer from 1 to 3 inclusive; which comprises alkylating an aminoalkanol using a benzaldehyde/aminoalkanol/ketone mixture in the presence of a platinum catalyst to give an alkyl substituted phenylmethylaminoalkanol; halogenating the alkanol using a halogenating agent to give a haloalkyl alkylbenzenemethanamine salt; treating the salt with substituted phenyl piperidinealkanenitrile or substituted phenyl pyrrolidinealkanenitrile in the presence of base and dimethyl sulfoxide to give a substituted phenyl substituted aminoalkyl piperidinealkanenitrile or substituted aminoalkyl pyrrolidinealkanenitrile; hydration of the nitrile to give the corresponding amide; and N-debenzylation of the amide followed by acetylation to give the compounds of formula I wherein Y is —CONH$_2$.

14 Claims, No Drawings

U.S. PATENT DOCUMENTS

| Patent No. | Date | Inventor | Class |
|---|---|---|---|
| 3,291,832 | 12/1966 | Kosak et al. | 260/580 |
| 3,361,819 | 1/1968 | Kosak et al. | 260/580 |
| 3,499,034 | 3/1970 | Gonzalez | 260/580 |
| 3,686,340 | 8/1972 | Patrick et al. | 260/672 |
| 3,751,462 | 8/1973 | McGurran et al. | 260/556 A |
| 3,855,237 | 12/1974 | Gatos | 260/326.8 |
| 3,868,403 | 2/1975 | Becker et al. | 260/471 R |
| 3,928,451 | 12/1975 | Krishnan | 260/580 |
| 3,950,393 | 4/1976 | Keck et al. | 260/471 R |
| 3,989,756 | 11/1976 | Fujise et al. | 260/580 |
| 4,020,107 | 4/1977 | Kosak | 260/580 |
| 4,022,830 | 5/1977 | Watts, Jr. | 260/559 R |
| 4,059,627 | 11/1977 | Kritzler et al. | 260/580 |
| 4,070,401 | 1/1978 | Hirai et al. | 260/580 |
| 4,098,789 | 7/1978 | Krapcho et al. | 544/299 |
| 4,127,607 | 11/1978 | Chignac et al. | 260/561 R |
| 4,166,072 | 8/1979 | Krapcho et al. | 260/558 P |
| 4,248,794 | 2/1981 | Fujii et al. | 564/133 |
| 4,639,524 | 1/1987 | Desai et al. | 546/229 |
| 4,760,183 | 7/1988 | Papenfuhs et al. | 564/398 |
| 4,795,813 | 1/1989 | Schwartz | 546/45 |
| 4,806,688 | 12/1989 | Inbasekaran et al. | 564/443 |
| 4,897,425 | 1/1990 | Zipperer et al. | 514/649 |
| 4,902,831 | 2/1990 | Mai et al. | 564/367 |
| 4,908,386 | 3/1990 | Finch et al. | 514/605 |
| 4,967,004 | 10/1990 | Maki et al. | 546/229 |
| 4,967,004 | 10/1990 | Maki et al. | 564/397 |
| 5,202,485 | 4/1993 | Maki et al. | 564/398 |

OTHER PUBLICATIONS

Morris Freifelder, Selective Hydrogenolysis Dehalogenation in the Presence of N-Benzyl Linkage, J. Organic Chemistry, 31, p. 3875 (1966).

Krichko, A. A., Catalysts for Hydrogenation Processes; Development and Use. Chemical Abstracts (100014m), vol. 78, (1973), p. 153.

Synthesis and Structure-Activity Relationships of a New Series of Antiarrhythmic Agents: Monobasic Derivatives of Disobutamide Journal of Medicinal Chemistry, 2158-2164, 1988 31.

PROCESS FOR THE PREPARATION OF HETEROCYCLIC ALKYLAMIDE DERIVATIVES

The present invention relates to a novel process for the preparation of heterocyclic alkylamide derivatives having the following formula:

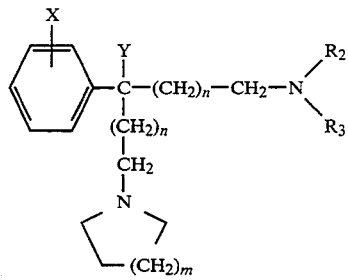

and the pharmaceutically acceptable acid addition salt thereof wherein X represents halo, alkyl having 1 to 6 carbon atoms, hydrido, trifluoromethyl, phenyl, or lower alkoxy having 1 to 6 carbon atoms; Y represents the group —CN or —CONH2; R2 represents alkyl having 1 to 6 carbon atoms; R3 represents acetyl, benzoyl, phenacetyl or trifluoroacetyl; m is the integer 1 or 2 and n is an integer from 1 to 3 inclusive; which comprises alkylating an aminoalkanol using a benzaldehyde/aminoalkanol/ketone mixture in the presence of a platinum catalyst to give an alkyl substituted phenylmethylaminoalkanol; halogenating said alkanol using a halogenating agent to give a haloalkyl alkylbenzenemethanamine salt; treating said salt with substituted phenyl piperidinealkanenitrile or substituted phenyl pyrrolidinealkanenitrile in the presence of base and dimethyl sulfoxide to give a substituted phenyl substituted aminoalkyl piperidinealkanenitrile or substituted aminoalkyl pyrrolidinealkanenitrile; hydration of the nitrile to give the corresponding amide; and N-debenzylation of the amide followed by acetylation to give the compounds of formula I wherein Y is —CONH2.

The process of the present invention is especially useful for preparing α-[2-[acetyl(1-methylethyl)amino]ethyl]-α-(2-chlorophenyl)-1-piperidinebutanamide which is described in U.S. Pat. No. 4,639,524.

α-[2-[Acetyl(1-methylethyl)amino]ethyl]-α-(2-chlorophenyl)-1-piperidinebutanamide is an active antiarrhythmic agent which has electrophysiologic effects in both the upper and lower parts of the heart. In addition to its potent antiarrhythmic utility, the subject compound possesses a desirable hemodynamic profile. A complete discussion of α-[2-[acetyl(1-methylethyl)amino]ethyl]-α-(2-chlorophenyl)-1-piperidinebutanamide usefulness as an antiarrhythmic agent is given in the "524" patent.

U.S. Pat. No. 4,639,524 discloses a process for preparing monobasic disobutamide derivatives having the following formula:

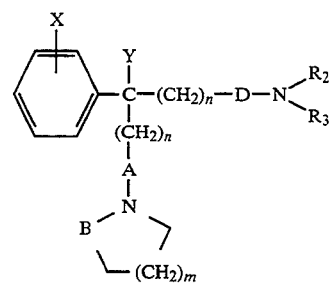

wherein X represents a halo, trifluoromethyl, phenyl, hydrogen, lower alkyl or lower alkoxy substituent; Y represents CN, CONH2, CON(R1)2 or CO2R1 where R1 represents lower alkyl; m is the integer 1 or 2 and n is an integer from 1 to 3 inclusive; R2 represents lower alkyl; R3 represents lower alkyl or acetyl, aroyl, phenacetyl or trifluoroacetyl; A, B and D are carbonyl or methylene such that when one of A, B or D is carbonyl the others are methylene and R3 is lower alkyl, whereas when R3 is acetyl, aroyl, phenacetyl or trifluoroacetyl, A, B, and D are methylene. This process is outlined in Schemes I to IV.

SCHEME (I)

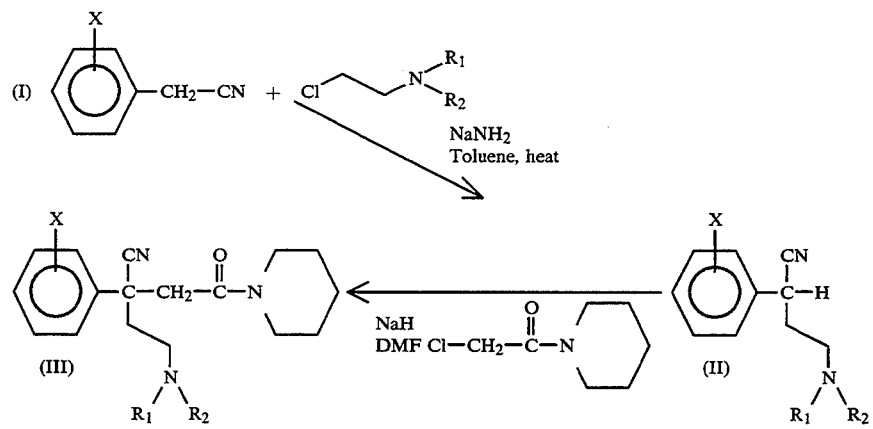

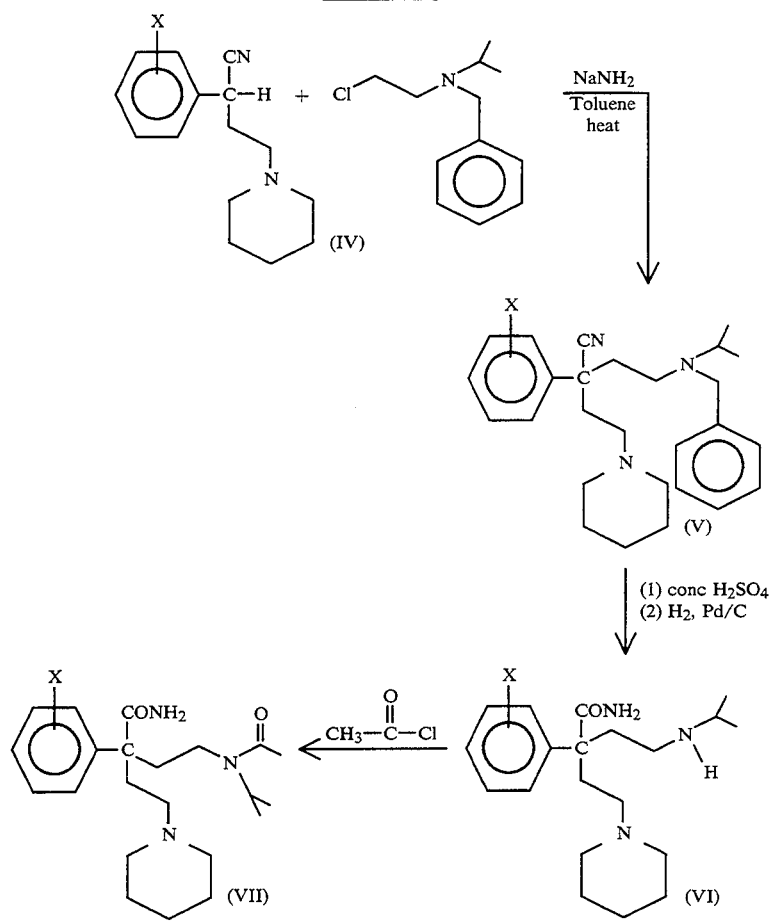
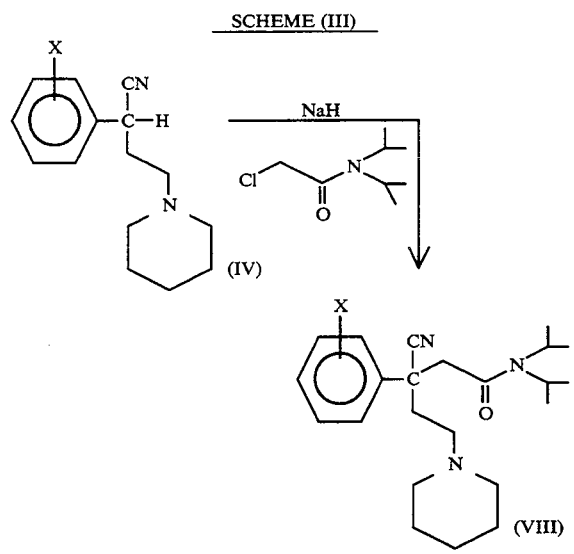
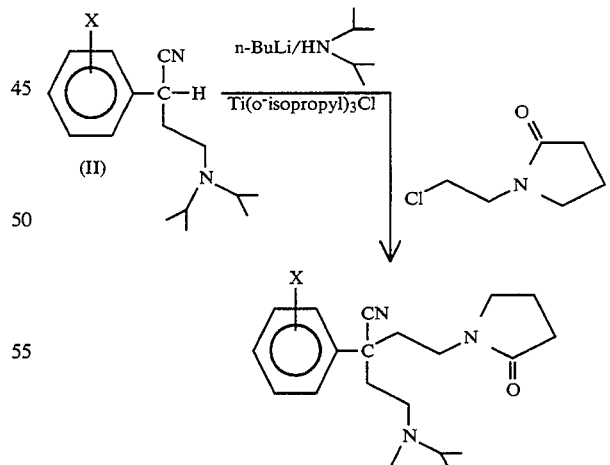
Reaction of the nitrile (II) with 1-(chloroacetyl) piperidine in the presence of sodium hydride provides the corresponding amide (III). The nitrile function may be replaced by an ester or a dimethyl amide function by using the ester or the dimethyl amide analog of (II) as a reactant. The intermediates (II) are broadly described in *J. Med. Chem.* 1980 23, 1102–1108.

Reaction of the nitrile (IV) with N-(2-chloroethyl)-N-(1-methylethyl)benzenemethanamine in the presence of sodium amide in toluene at 85° C. for 1 hour affords the corresponding nitrile (V). Hydration of the nitrile (V) with sulfuric acid followed by catalytic hydrogenation provides the corresponding amide (VI). Acylation of (VI) with acetyl chloride or other acyl chlorides such as trifluoroacetyl, aroyl or phenacetyl yields the desired acylated amide (VII).

Treatment of the nitrile (IV) with sodium hydride in N,N-dimethylformamide followed by 1-chloro-N,N-bis-(1-methylethyl)acetamide affords the nitrile amide VIII as shown in Scheme III.

Reaction of the nitrile II with lithium diisopropylamide in THF followed by treatment with tris (isopropoxy)titanium chloride [Helv. Chim. Acta., 64, 357 (1981)] and subsequent condensation with 1-(2-chloroethyl)pyrrolidin-2-one produces the nitrilepyrrolidone IX as shown in Scheme IV.

The present invention relates to a process for the preparation of alkylamides having the following formula:

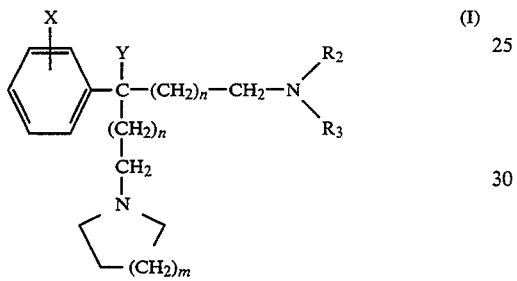

(I)

and the pharmaceutically acceptable acid addition salt thereof wherein X represents halo, alkyl having 1 to 6 carbon atoms, hydrido, trifluoromethyl, phenyl, or lower alkoxy having 1 to 6 carbon atoms; Y represents the group —CN or —CONH$_2$; R$_2$ represents alkyl having 1 to 6 carbon atoms; R$_3$ represents acetyl, benzoyl, phenacetyl or trifluoroacetyl; m is the integer 1 or 2 and n is an integer from 1 to 3 inclusive; which comprises:

(a) alkylation of an aminoalkanol using, sequentially, benzaldehyde in the presence of an alkanol solvent, platinum catalyst and hydrogen followed by reductive alkylation using a ketone in the presence of a platinum catalyst and hydrogen to give an alkyl substituted phenylmethylamino alkanol;

(b) halogenating the alkyl substituted phenylmethyl aminoalkanol of step (a) using a halogenating agent in the presence of an aprotic solvent to give a N-haloalkyl-N-alkylbenzenemethanamine salt;

(c) alkylating a compound of the formula:

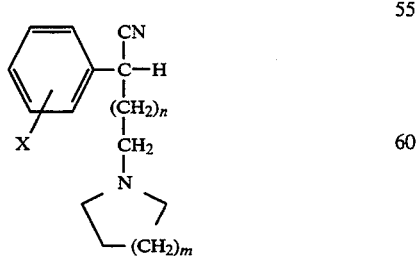

wherein X represents a halo, alkyl having 1 to 6 carbon atoms, hydrido, trifluoromethyl, phenyl or lower alkoxy having 1 to 6 carbon atoms; m is the integer 1 or 2 and n is an integer from 1 to 3 inclusive with the product of step (b) in the presence of a base and dimethyl sulfoxide to give a compound of the formula:

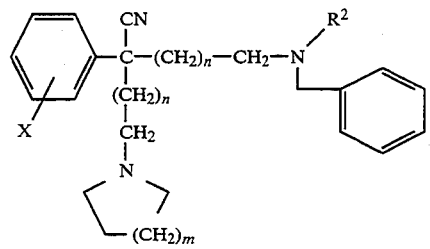

wherein R$_2$, X, m and n have the meaning defined above;

(d) hydrating the product of step (c) in the presence of a mineral acid to give a compound of the formula:

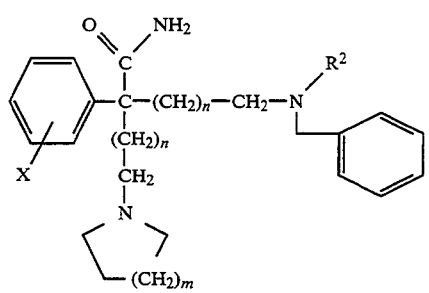

wherein R$_2$, X, m and n have the meaning defined above;

(e) debenzylating the product of step (d) using a supported palladium catalyst or a supported palladium (sulfited) catalyst with the proviso that when X is halo the supported palladium catalyst or the supported palladium (sulfited) catalyst is used in conjunction with a modifier to give a compound of the formula:

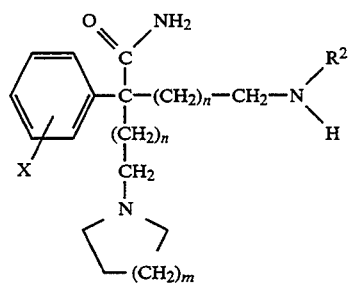

wherein R$_2$, X, m and n have the meaning defined above;

(f) acylating the product of step (e) using an anhydride having the following formula:

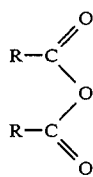

wherein R is methyl, phenyl, phenylmethyl or trifluoromethyl to give the compound of formula I wherein $R_3$ represents acetyl, benzoyl, phenacetyl or trifluoroacetyl, $R^2$ represents alkyl having 1 to 6 carbon atoms, X represents halo, alkyl having 1 to 6 carbon atoms, hydrido, trifluoromethyl, phenyl, or lower alkoxy having 1 to 6 carbon atoms.

The present invention also relates to a process for preparing α-[2-[acetyl(1-methylethyl)amino]ethyl]-α-(2-chlorophenyl)-1-piperidinebutanamide which has the following formula:

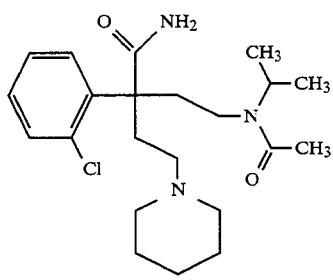

and comprises the steps of:

(a) alkylating 2-aminoethanol using benzaldehyde and ethanol in the presence of a platinum catalyst and hydrogen followed by reductive alkylation using acetone in the presence of a platinum catalyst and hydrogen to give 2-[(1-methylethyl)(phenylmethyl) amino]ethanol;

(b) halogenating 2-[(1-methylethyl) (phenylmethyl) amino]ethanol using a halogenating agent in the presence of an aprotic solvent to give N-(2-chloroethyl)-N-(1-methylethyl)benzenemethanamine, monohydrochloride;

(c) alkylating α-(2-chlorophenyl)-1-piperidine butanenitrile with N-(2-chloroethyl)-N-(1-methylethyl)benzenemethanamine, monohydrochloride in the presence of base and dimethyl sulfoxide to give α-(2-chlorophenyl)-α-[2-[(1-methylethyl) (phenylmethyl)amino]ethyl]-1-piperidinebutane nitrile;

(d) hydrating α-(2-chlorophenyl)-α-[2-[(1-methylethyl) (phenylmethyl)amino]ethyl]-1-piperidenebutanenitrile in the presence of mineral acid to give α-(2-chlorophenyl)-α-[2-[(1-methylethyl) (phenylmethyl)amino]ethyl]-1-piperidinebutanamide;

(e) debenzylating α-(2-chlorophenyl)-α-[2-[(1-methylethyl)(phenylmethyl)amino]ethyl]-1-piperidinebutanamide using a supported palladium catalyst or a supported palladium (sulfited) catalyst in presence of a modifier to give α-(2-chlorophenyl)-α-[2-[(1-methylethyl)amino]ethyl]-1-piperidinebutanamide; and (f) acetylating α-(2-chlorophenyl)-α-[2-[(1-methylethyl)amino]ethyl]-1-piperidinebutanamide in the presence of acetic anhydride to give α-[2-[acetyl(1-methylethyl)amino]ethyl]-α-(2-chlorophenyl)-1-piperidinebutanamide.

This process is outlined by Scheme A.

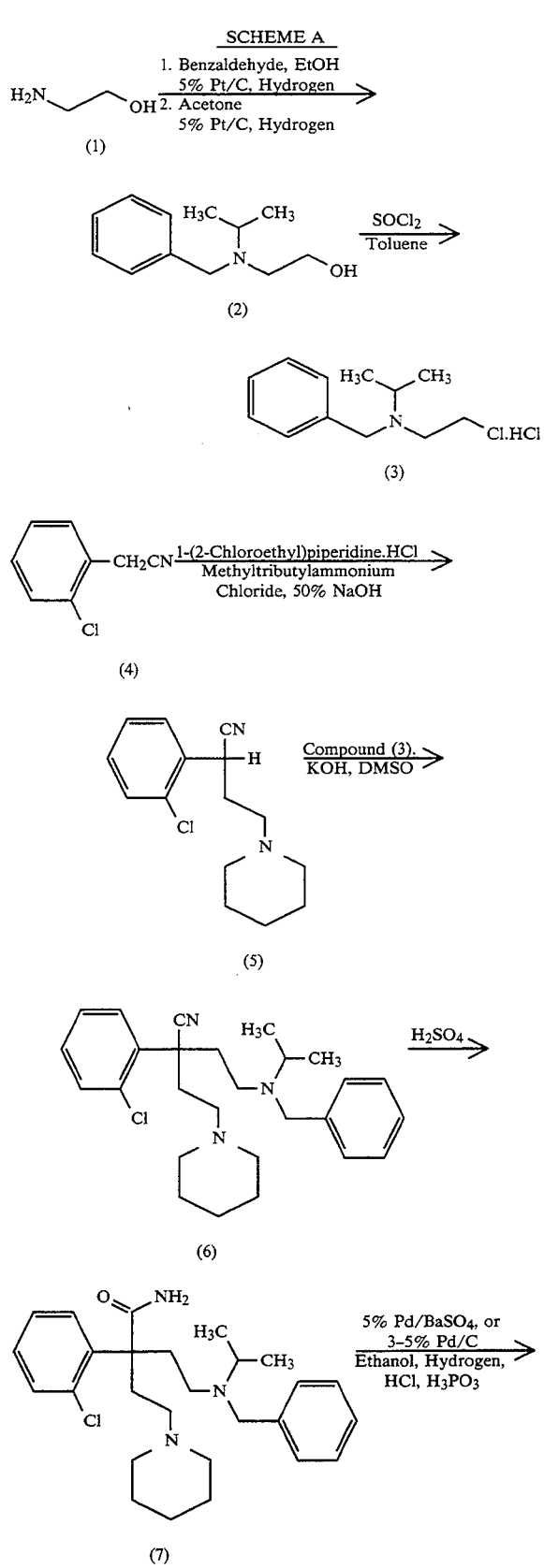

-continued
SCHEME A

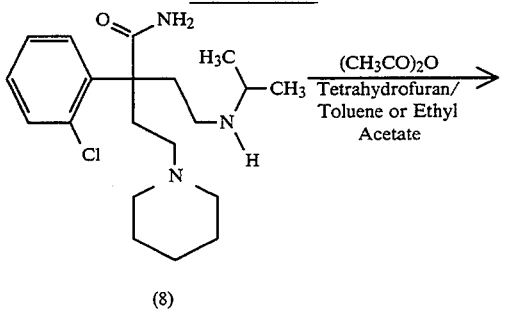

(8)

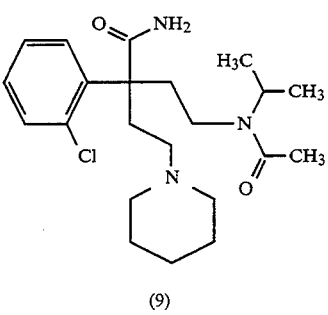

(9)

The starting material for the process of this invention is commercially available aminoalkanol. Suitable aminoalkanols for the practice of this invention are exemplified by 2-aminoethanol, 3-aminopropanol and 4-aminobutanol with 2-aminoethanol being preferred.

The reductive alkylation step (step (a) of the process) is carried out using benzaldehyde or substituted benzaldehyde and the aminoalkanol in the presence of an alkanol solvent using a platinum-on-carbon catalyst at a constant pressure of atmospheric to 100 psig of hydrogen and at a temperature ranging from 0° C. to 60° C. The second alkylation step is carried out by adding the dialkyl ketone to the reaction mixture and continuing at a constant pressure of atmospheric to 100 psig of hydrogen and at a temperature ranging from 0° C. to 60° C. Suitable alkanol solvents are exemplified by methanol, ethanol, isopropanol and butanol with ethanol being preferred. The platinum-on-carbon catalyst is characterized by having poor dispersion of the platinum metal on the support. In this case a catalyst that has poor dispersion is characterized by large clusters of metal unevenly distributed on the support. It is this physical characteristic—poor dispersion—that accounts for the desired level of activity and selectivity A "Use Test" which is described below, is performed on each lot of catalyst to determine its suitability for this step of the process. A catalyst which provides 98.5 to 99.5% purity without further purification of final product is considered suitable.

5% Platinum-on-Carbon Use Test: To a 500-mL Parr ® bottle are charged 18.3 g of 2-aminoethanol, 100 mL of 3A ethanol (190 proof) and 32.5 g of benzaldehyde. A mild exotherm is observed. The reaction mixture is agitated for 30 min. To the reaction mixture is charged 2.0 g of 5% Pt/C (51% H$_2$O, 1.0 g dry 5% Pt/C). The bottle is sealed, and the reaction mixture is hydrogenated at 60 psig hydrogen pressure and ambient temperature for 10 h. After 10 h the bottle is opened and 100 mL of acetone is charged to the reaction mixture. The bottle is sealed and the reaction is continued at 60 psig and ambient temperature for 42 h. The reaction mixture is filtered, and the filtrate is sampled for GLC analysis. The peaks for solvent, isopropanol, benzyl alcohol and toluene are removed, and the remaining peaks are area normalized. A typical assay for the desired product, 2-[(1-methylethyl)(phenylmethyl)amino]ethanol, is 98.5 to 99.5%.

The halogenation (step (b) of the process) reaction is carried out at a temperature ranging from 0° C. to 110° C. with a temperature ranging from 35° C. to 40° C. being preferred using a halogenating agent in the presence of an aprotic solvent. Suitable halogenating agents are exemplified by thionyl chloride, phosphorus trichloride, phosphorus pentachloride, phosphorus oxychloride with thionyl chloride being preferred. Suitable aprotic solvents are toluene, xylene, and N,N-dimethylformamide with toluene being preferred.

Alkylation of the nitrile (step (c) of the process) is carried out in the presence of base and an aprotic solvent. Suitable bases are exemplified by sodium hydroxide, potassium hydroxide and lithium hydroxide, with potassium hydroxide being preferred. Suitable aprotic solvents are exemplified by dimethyl sulfoxide, and tetrahydrofuran, with dimethyl sulfoxide being preferred. The α-(substituted phenyl)heterocyclic alkylnitrile of this step is prepared by reacting a substituted benzeneacetonitrile wherein the substituent can be selected from halo, alkyl having 1 to 6 carbon atoms, hydrido, trifluoromethyl, phenyl, or lower alkoxy having 1 to 6 carbon atoms with a haloalkylpiperidine or a haloalkylpyrrolidine. A detailed description of this procedure is provided later.

Hydration of the product of step (c) of the process is carried out in the presence of a mineral acid. Suitable mineral acids are exemplified by hydrogen chloride, hydrogen bromide, hydrogen fluoride, sulfuric acid, acetic acid and trifluoroacetic acid. Sulfuric acid is preferred.

Debenzylation of the product of step (d) of the process is carried out in the presence of hydrochloric acid and a supported palladium catalyst or a supported palladium (sulfited) catalyst at temperatures ranging from 0° C. to 100° C. and hydrogen pressures from 0 to 100 psig. A temperature ranging from 25° C. to 45° C. and hydrogen pressures from 1 to 10 psig are preferred. Suitable supports are exemplified by carbon, barium sulfate, calcium carbonate, alumina, silca and strontium carbonate. When the compound of formula I wherein X is halo is desired, the supported palladium catalyst or the supported palladium (sulfited) catalyst must exhibit a particular physical characteristic and be used in conjunction with a catalyst modifier. The desired physical characteristic is characterized by highly reduced palladium dispersed on the surface of the support. The catalyst modifier is phosphorous acid. The catalyst modifier can also be selected from morpholine, N-alkylmorpholine, piperazine or N-alkylpiperazine with phosphorous acid being preferred. These requirements are necessary in order that the desired activity and selectivity (removal of the benzyl group without any appreciable removal of the halo group) are achieved. In order to determine the ratio of palladium catalyst to catalyst modifier, a "Use Test", which is described below, is performed. A ratio of palladium catalyst to modifier which provides a final product in 98%+ purity is acceptable.

3-5% Pd/C Catalyst Use Test: To a 250-mL Parr ® bottle are charged 8.0 g of α-(2-chlorophenyl)-α-[2-[(1-methylethyl)(phenylmethyl)amino]ethyl]-1-piperidinebutanamide, 0.912 g of 3% Pd/C (57% H$_2$O), 6.0 mL of a freshly prepared solution of 0.202 g of H₃PO₃ in 250 mL of 3A ethanol (190 proof), 80 mL of 3A ethanol (190 proof), and 3.2 mL of concentrated hydrochloric acid. The bottle is sealed, and the reaction mixture is hydrogenated at 5 psig hydrogen pressure and 40° C. for 23.5 h. The reaction mixture is filtered, and the filtrate is sampled for HPLC analysis. The solvent peaks are removed, and the remaining peaks are area normalized. A typical assay for the reaction mixture is 98%+ α-(2-chlorophenyl)-α-[2-[(1-methylethyl)amino]ethyl]-1-piperidinebutanamide, 0.30% to 0.40% of the deschloro compound and 0.0% to 1.0% of the starting material.

As used herein, the term "alkyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenyloxy, 3-methylbutoxy, 1-methylbutoxy, 1-ethylpropoxy, 2,2-dimethylpropoxy, 1,1-dimethylpropoxy, hexenyloxy, and 4-methylpentoxy.

As used herein the term "halo" embraces halogen atoms. Illustrative of such atoms are chloro (Cl), fluoro (F), bromo (Br) and iodo (I).

The present invention provides a safe, convenient and cost effective manufacturing process for the production of the alkylamide derivatives of formula I. It particularly provides a safe, convenient and cost effective manufacturing process for the production of α-[2-[acetyl(1-methylethyl)amino]ethyl]-α-(2-chlorophenyl)-1-piperidinebutanamide. Its safety is demonstrated by the elimination of potentially hazardous solvents. The subject compound is prepared using acetic anhydride in place of acetyl chloride and triethylamine. Also the process utilizes a tetrahydrofuran-toluene or ethyl acetate solution instead of methylene chloride solution. Its convenience is demonstrated by the synthetic route comprising a limited number of steps. Its cost effectiveness is demonstrated by the final product being produced in high yield and high quality.

In addition to the above described advantages, the processes of the present invention also possesses a distinct advantage over the process described in the "524" patent. The starting material for step (b) of the instant process 2-[(1-methylethyl)(phenylmethyl) amino]ethanol is prepared by a one pot, two-step route which begins with commercially available starting materials. The 2-[(1-methylethyl)(phenylmethyl) amino]ethanol is obtained in higher purity with no distillation or other purification step required. It therefore can be used directly in the next step.

The following examples further illustrate the invention. All temperatures are degrees Celsius unless otherwise noted.

Infrared (IR) spectra are recorded on a Perkin-Elmer® 681 spectrophotometer. Nuclear magnetic resonance (NMR) spectra are obtained on a Varian® VXR-200 spectrometer using tetramethylsilane as internal standard. Elemental analyses are obtained using a Control Equipment Model 240XA Elemental Analyzer (CHN) and a Mettler potentiometric titration system (total Cl and Cl⁻). Differential scanning calorimetry (DSC) analyses are obtained using a DuPont® Model 9900 thermal analysis system.

Chemical reactions are monitored by gas chromatography (GC) or thin layer chromatography (TLC) on Macherey-Nagel® SIL G-25 UV₂₅₄silica gel plates. Chemical intermediates are analyzed by GC or high performance liquid chromatography (HPLC). Qualitative estimates of purity are made based upon integration of the area under the peaks in the GC or HPLC chromatograms.

| | GC Method A |
|---|---|
| Column: | Methyl Silicone (15 m × 0.25 mm × 0.25 micron film thickness) |
| Temperature: | 40–280° C. at 30° C./min with a 2-min hold at 280° C. |
| Flow Rate: | 1 mL/min (helium) |
| Detection: | Flame ionization |
| | GC Method B |
| Column: | Methyl Silicone (10 m × 0.53 mm) |
| Temperature: | 50–275° C. at 70° C./min with a 2-min hold at 275° C. |
| Flow Rate: | 20 mL/min (helium) |
| Detection: | Flame ionization |
| | GC Method C |
| Column: | Methyl Silicone (10 m × 0.53 mm) |
| Temperature: | 70–275° C. at 70° C./min with a 6-min hold at 275° C. |
| Flow Rate: | 20 mL/min (helium) |
| Detection: | Flame ionization |
| | TLC Method A |
| Mobile Phase: | Cyclohexane/Isopropanol/Ammonium Hydroxide, 77.5/20.0/2.5 (v/v/v) |
| Visualization: | I₂ and SWUV |
| | TLC Method B |
| Mobile Phase: | Cyclohexane/Isopropanol/Ammonium Hydroxide, 70/28/2 (v/v/v) |
| Visualization: | I₂ and SWUV |
| | HPLC Method |
| Column: | Partisil 10 ODS-3 |
| Mobile Phase: | Acetonitrile/Triethylamine Phosphoric Acid Buffer (pH 3), 4/96 (v/v) |
| Flow Rate: | 1.5 mL/min |
| Detection: | UV at 210 nm |

EXAMPLE 1

Preparation of 2-[(1-Methylethyl)(phenylmethyl)amino]ethanol

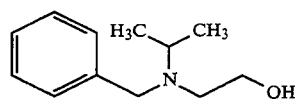

A dry, nitrogen-purged hydrogenation vessel was charged with 94 L of 3A ethanol, (95%), 18.3 kg of 2-aminoethanol and 32.5 kg of benzaldehyde. The reaction was stirred for 30 min and a slurry of 2.0 kg of 5% platinum-on-carbon (50% water-wet) catalyst in 6 L of 3A ethanol, (95%), was charged. The mixture was stirred rapidly and hydrogenated at a constant pressure of 60 psig of hydrogen at 25° to 40° C. until the reaction was complete as indicated by hydrogen uptake and gas chromatographic analysis. The hydrogen was vented, a nitrogen atmosphere was applied, and a mole ratio of 3.5 to 7:1 of acetone based on 2-aminoethanol was charged to the reaction. The mixture was stirred rapidly and hydrogenated at a constant pressure of 60 psig of hydrogen at 25° to 30° C. until the reaction was complete as indicated by hydrogen uptake and gas chromatographic analysis. The hydrogen was vented, and a nitrogen atmosphere was applied to the reaction vessel. The 5% platinum-on-carbon (50% water-wet) catalyst was removed by filtration through a layer of powdered cellulose. The catalyst was washed with 20 L of 3A ethanol (95%) and the wash was combined with the filtrate. The solvent was removed by distillation under reduced pressure.

The residual oils from four such preparations were combined to give 226.5 kg (98.3% of theory based on 2-aminoethanol) of title compound 2-[(1-methylethyl)(phenylmethyl)amino]ethanol. These residual oils can be used as is in the next step. The purity of the title compound was estimated to be >98% based on GC Method A.

EXAMPLE 2

Preparation of N-(2-Chloroethyl)-N-(1-methylethyl) benzenemethanamine, monohydrochloride

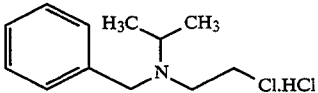

A reaction vessel under a nitrogen atmosphere was charged with 503 L of toluene and 51.9 kg of thionyl chloride. Nitrogen was sparged through the stirred solution, and 76.7 kg of 2-[(1-methylethyl) (phenylmethyl)amino]ethanol (product of Example 1) was added at 30° to 40° C. After the addition was complete, the temperature was maintained at 35° to 40° C. After 4 h, 6.2 L of isopropyl alcohol was added. After nitrogen sparging for at least 9.5 h at ≦40° C., the mixture was allowed to cool to about 25° C. with stirring. The stirred slurry was cooled to less than 10° C. for at least 1 h. The resulting solid was collected by filtration and washed with 114 L of toluene. The solid was dried at about 35° C. to give 93.3 kg (94.7%) of the title product N-(2-chloroethyl)-N-(1-methylethyl)benzenemethanamine, monohydrochloride.

Analysis calcd for $C_{12}H_{19}Cl_2N$: C,58.07; H,7.72; Cl,28.57; N,5.64. Found: C,57.72; H,7.80; Cl,28.67; N,5.63. mp 129°–134° C.

EXAMPLE 3

Preparation of α-(2-Chlorophenyl)-1-piperidinebutanenitrile

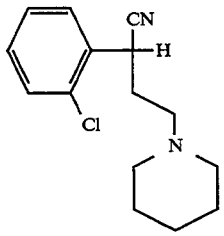

A reaction vessel under a nitrogen atmosphere containing 74.0 kg of 1-(2-chloroethyl)piperidine, monohydrochloride at 10° C. was charged with 255.4 kg of sodium hydroxide solution (50% w/w). The reaction was warmed to 30° to 35° C. and 67.0 kg of 2-chlorobenzeneacetonitrile and 1.4 kg of methyltributylammonium chloride (75% w/w in water) were added. The reaction was stirred at 40° C. for 6 h and then heated to 60° C. for at least 6 h. When the reaction was completed as indicated by gas chromatographic analysis, the reaction mixture was cooled to 25° C. The reaction mixture was diluted with 335 L of water and 134 L of toluene and stirred for 30 min. After separation of the layers, the organic phase was extracted with 275 L of hydrochloric acid (2N). The acidic extract was washed twice with 50 L of toluene, basified with 30 L of sodium hydroxide solution (50% w/w) to a pH>12 and extracted twice with a total of 368 L of heptane. The combined organic phase was washed with 50 L of water and filtered through a layer of diatomaceous earth. The filtrate was dried by azeotropic distillation. The solvent was removed by distillation under reduced pressure to give 104.5 kg (90.0%) of the title product α-(2-chlorophenyl)-1-piperidinebutanenitrile as an oil. Analysis calcd for $C_{15}H_{19}ClN_2$: C,68.56; H,7.29; Cl,13.49; N,10.66. Found: C,69.64; H,7.53; Cl,12.45; N,9.75. The crude product (oil) was carried forward to the next step without purification. The purity of the title compound was estimated to be 98% based on GC Method B.

EXAMPLE 4

Preparation of α-(2-Chlorophenyl)-α-[2-[(1-methylethyl)(phenylmethyl)amino]ethyl]-1-piperidinebutanenitrile

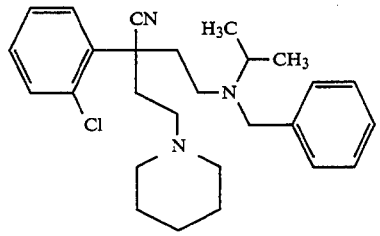

To a reaction vessel under a nitrogen atmosphere was charged 35.0 kg of pulverized potassium hydroxide (90%) and 34.0 L of dimethyl sulfoxide. A solution of 29.5 kg of α-(2-chlorophenyl)-1-piperidinebutanenitrile (product of Example 3) in 23 L of dimethyl sulfoxide was added while maintaining the temperature below 25° C. A solution of 30.7 kg of N-(2-chloroethyl)-N-(1-methylethyl)benzenemethanamine, monohydrochloride in 112 L of dimethyl sulfoxide was added while maintaining the temperature below 20° C. The mixture was stirred at 25° C. until the reaction was complete as indicated by gas chromatographic analysis (GC Method C). The mixture was cooled and diluted with 122 L of heptane and 200 L of water. The layers were separated, and the organic phase was filtered through a layer of diatomaceous earth. The filter cake was washed with 40 L of heptane. The combined organic phase was washed twice with 70 L of water and dried by azeotropic distillation. The solvent was removed by distillation under reduced pressure to give 49.4 kg (100.0%) of the title product α-(2-chlorophenyl)-α-[2-[(1-methylethyl)(phenylmethyl)amino]ethyl]-1-piperidinebutanenitrile as an oil. Analysis calcd for $C_{27}H_{36}ClN_3$: C,74.03; H,8.28; Cl,8.09; N,9.59. Found: C,73.35; H,8.36; Cl,7.27; N,9.15. The crude product (oil) was carried forward to the next step without purification. The purity of the title compound was estimated to be >85% based on GC Method C.

EXAMPLE 5

Preparation of
α-(2-Chlorophenyl)-α-[2-[(1-methylethyl)
(phenylmethyl)amino]ethyl]-1-piperidinebutanamide

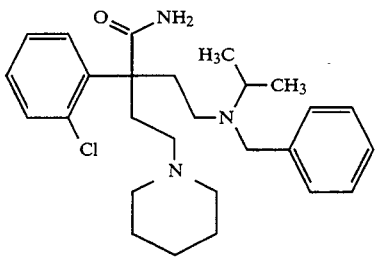

A nitrogen atmosphere was applied to a reaction vessel containing 109.3 L of sulfuric acid (96% w/w) which was warmed to 70° C. with stirring. Heating was discontinued, and 89.2 kg of α-(2-chlorophenyl)-α-[2-[(1-methylethyl)(phenylmethyl)amino]ethyl]-1-piperidinebutanenitrile (product of Example 4) was added at a rate such that the temperature was maintained at 80°-85° C. The reaction mixture was stirred at 80°-85° C. for 2.5 h and cooled to 75° C. The reaction mixture was added to a cooled and stirred mixture of 322 L of water and 219 L of toluene at 5° C. at a rate such that the temperature did not exceed 30° C. An additional 127 L of water was added to rinse the reactor. The mixture was cooled to 5° C. and basified to pH>12 with 219 L of sodium hydroxide solution (50% w/w) while maintaining the temperature below 35° C. Near the end of the base addition, the mixture was allowed to warm to 45° C. and stirred for 15 min. After separation of the layers, the aqueous phase was maintained at 45° C. and extracted with two 126-L portions of toluene. The organic phases were combined using 126 L of toluene. The combined organic phase was washed with 126 L of water at 45° C. The solution was cooled to 25° C. and stirred with 64.3 kg of neutral alumina for 1 h. The slurry was filtered through a layer of diatomaceous earth, and the filter cake was washed with 126 L of toluene. Alternatively, the solution may be passed through a bed of neutral alumina followed by a toluene wash of the bed. The solvent was removed by distillation under reduced pressure, and the residue was dissolved in 322 L of heptane by heating to reflux. The solution was allowed to cool to 25° C. with stirring, and the resulting slurry was cooled to less than 10° C. The solid was collected by filtration and washed twice with 200 L of heptane. The solid was dried under vacuum at 35 to 40° C. to give 65.0 kg (70.0%) of the title product α-(2-chlorophenyl)-α-[2-[(1-methylethyl)(phenylmethyl) amino]ethyl]-1-piperidinebutanamide. Analysis calcd for $C_{27}H_{38}ClN_3O$: C,71.11; H,8.40; Cl,7.77; N,9.21. Found C,71.09; H,8.50; Cl,7.94; N,9.17. mp 104°-111° C. The purity of the title compound was estimated to be >95% based on TLC Method A.

EXAMPLE 6

Preparation of
α-(2-Chlorophenyl)-α-[2-[(1-methylethyl)
amino]ethyl]-1-piperidinebutanamide

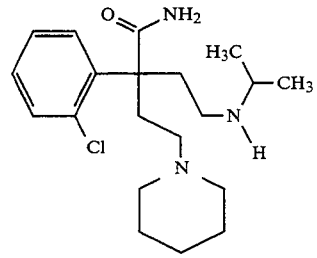

A hydrogenation vessel under a nitrogen atmosphere was charged with 10 to 12.5 kg of 5% palladium-on-barium sulfate catalyst, or 1.25-2.5 kg of 3 to 5% palladium-on-carbon catalyst (50% water-wet), or 1.25-2.5 kg of palladium-on-carbon (sulfited) catalyst, 25.0 kg of α-(2-chlorophenyl)-α-[2-[(1-methylethyl) (phenylmethyl)amino]ethyl]-1-piperidinebutanamide (product of Example 5) 15 g to 50 g of phosphorous acid, 248 L of 3A ethanol, (95%), and 10 L of hydrochloric acid (12N). The mixture was stirred rapidly and hydrogenated at a constant pressure of 3 to 6 psig of hydrogen at 25°-40° C. until the reaction was complete as indicated by high performance liquid chromatographic analysis. A nitrogen atmosphere was applied to the vessel, and the palladium catalyst was removed by filtration through a layer of powdered cellulose. The catalyst was washed with 50 L of 3A ethanol, (95%), and the wash was combined with the filtrate.

The filtrates from two similar runs on a total of 50.0 kg of α-(2-chlorophenyl)-α-[2-[(1-methylethyl) (phenylmethyl)amino]ethyl]-1-piperidinebutanamide were combined, and the solvent was removed by distillation under reduced pressure. The residue was dissolved in 423 L of water, and the solution was filtered through diatomaceous earth. To the filtrate was added 146 L of toluene and 222 L of tetrahydrofuran. Sodium hydroxide solution (50% w/w), 15.2 L, was then added over 15 min. The mixture was warmed to 60° C. and was stirred for 30 min. The aqueous layer was separated and to it was added 91 L of toluene and 91 L of tetrahydrofuran. This mixture was stirred at 60° C. for 30 min. The aqueous layer was separated and the organic layer was combined with the first organic layer while maintaining the temperature at 60° C. The warm organic solution was filtered through diatomaceous earth, and the filter cake was washed with 100 L of a 50% toluene/50% tetrahydrofuran (v/v) solution at 60° C. The solvents were partially removed from the combined organic phases by distillation at atmospheric pressure to a temperature of 95°-110° C. Heptane, 237 L, was added to the concentrated solution. The solution was cooled to 25° C. with stirring, and the resultant slurry was cooled to 10° C. and maintained for 1 h. The solid was collected by filtration and washed with 100 L of a 50% toluene/50% heptane (v/v) solution at 10° C. The product was dried under vacuum at 25° to 50° C. to give 36.2 kg (90.2%) of the title product α-(2-chlorophenyl)-α-[2-[(1-methylethyl)amino]ethyl]-1-piperidine butanamide.

The title product with substantial yellow color may be decolorized using the following procedure. The product, 65.5 kg, was dissolved in a solution of 29.7 L of hydrochloric acid, (12N) in 326 L of water. The solution was treated with 3.9 kg of activated carbon for 1 h. The activated carbon was removed by filtration through diatomaceous earth, and the cake was washed with 40 L of water. The filtrate was diluted with 413 L of water and basified to pH>12 by adding 20.4 L of sodium hydroxide solution (50% w/w). The precipitated solid was isolated by filtration and washed with 120 L of water. The product was dried under vacuum at 25°–50° C. to give 65.5 kg (100%) of α-(2-chlorophenyl)-α-[2-[(1-methylethyl)amino]ethyl]-1-piperidinebutanamide. Analysis calcd for $C_{20}H_{32}ClN_3O$: C,65.64; H,8.81; Cl,9.69; N,11.48. Found: C,64.50; H,8.76; Cl,9.40; N,11.31. mp 134°–137° C. The purity of the title compound was estimated to be >95% based on TLC Method B.

EXAMPLE 7

Preparation of α-[2-[Acetyl (1-methylethyl)amino]ethyl]-α-(2-chlorophenyl)-1-piperidinebutanamide

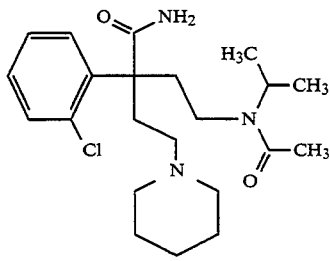

To a reaction vessel under a nitrogen atmosphere was charged 70.2 kg of α-(2-chlorophenyl)-α-[2-[(1-methylethyl)amino]ethyl]-1-piperidinebutanamide (the product of Example 6) 208.1 L of tetrahydrofuran, and 208.1 L of toluene. The solution was stirred and 21.0 kg of acetic anhydride was added at a rate such that the temperature was maintained at 25° C. The mixture was stirred at 25° C. until the reaction was complete as indicated by thin layer chromatographic analysis (Method B). Methanol, 28.1 L, was added while maintaining a temperature of 30° C. A solution of 21.1 kg of sodium hydroxide solution (50% w/w) in 126.5 L of water was added while maintaining a temperature of 30° C. The reaction mixture was stirred at 30° C. for 30 min. The lower aqueous phase was separated and to the organic phase was added a solution of 21.1 kg of sodium hydroxide solution (50% w/w) in 126.5 L of water while maintaining a temperature of 30° C. The reaction mixture was stirred at 30° C. for 30 min. The lower aqueous layer was separated, and the organic phase was passed through a filter containing 28.1 kg of potassium carbonate. The potassium carbonate was washed with 326 L of a 50% toluene/50% tetrahydrofuran (v/v) solution, and the wash was combined with the filtrate. The solution was concentrated by distillation at reduced pressure. Ethyl acetate, 625 L, was added to the distillation residue, and the mixture was heated to effect dissolution. Ethyl acetate, 155 L, was removed by distillation at atmospheric pressure, and the remaining solution was filtered. Additional quantities of ethyl acetate may be used if the excess is removed by distillation and a solvent to substrate ratio of approximately seven is maintained. Alternatively, the required quantity of ethyl acetate may be used without the need for distillative removal.

The solution was cooled to 22° C., and after crystallization began the mixture was maintained at this temperature for at least one hour. The mixture was cooled to 5° C. and maintained for one hour. The solid was isolated by filtration and washed with 173 L of ethyl acetate. The product was dried under vacuum at 35°–75° C. to give 65.3 kg (83.4%) of the title product α-[2-[acetyl(1-methylethyl)amino]ethyl]-α-(2-chlorophenyl)-1-piperidinebutanamide.

If the title product does not meet the color specification, it may be decolorized using the following procedure. A 15-kg portion of the product was dissolved in 90 L of ethyl acetate at 75° C. A slurry of 1.5 kg of activated carbon in 2 L of ethyl acetate was added, and the mixture stirred for 30 min. The activated carbon was removed by filtration through diatomaceous earth. The solution was cooled to 25° C. with stirring, and the resulting slurry was then directly cooled to 10° C. The solid was isolated by filtration and washed with 48 L of ethyl acetate. The product was dried under vacuum at 35°–75° C. to give 12.1 kg (80.6%) of α-[2-[acetyl(1-methylethyl)amino] ethyl]-α-(2-chlorophenyl)-1-piperidinebutanamide.

Analysis calcd for $C_{22}H_{34}ClN_3O_2$: C,64.77; H,8.40; Cl,8.69; N,10.30. Found: C,64.70; H,8.54; Cl,8.84; N,10.34. mp 141°–147° C.

What we claim is:

1. A process for preparing a compound of the formula

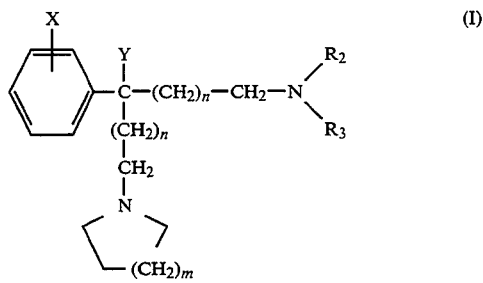

and the pharmaceutically acceptable acid addition salt thereof wherein X represents halo, alkyl having 1 to 6 carbon atoms, hydrido, trifluoromethyl, phenyl, or lower alkoxy having 1 to 6 carbon atoms; Y represents the group —CN or —CONH$_2$; R$_2$ represents alkyl having 1 to 6 carbon atoms; R$_3$ represents acetyl, benzoyl, phenacetyl or trifluoroacetyl; m is the integer 1 or 2 and n is an integer from 1 to 3 inclusive; which comprises:

(a) alkylation of an aminoalkanol using, sequentially, benzaldehyde in the presence of an alkanol solvent, platinum catalyst and hydrogen followed by reductive alkylation using a ketone in the presence of a platinum catalyst and hydrogen to give an alkyl substituted phenylmethylamino alkanol;

(b) halogenating the alkyl substituted phenylmethyl aminoalkanol of step (a) using a halogenating agent in the presence of an aprotic solvent to give a N-haloalkyl-N-alkylbenzenemethanamine salt;

(c) alkylating a compound of the formula:

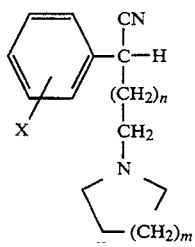

wherein X represents halo, alkyl having 1 to 6 carbon atoms, hydrido, trifluoromethyl, phenyl or lower alkoxy having 1 to 6 carbon atoms; m is the integer 1 or 2 and n is an integer from 1 to 3 inclusive with the product of step (b) in the presence of a base and dimethyl sulfoxide to give a compound of the formula:

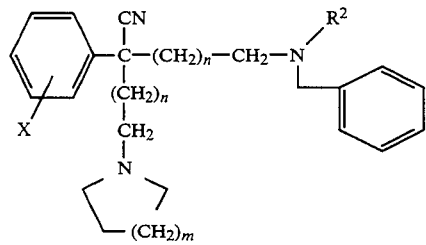

wherein R₂, X, m and n have the meaning defined above;

(d) hydrating the product of step (c) in the presence of a mineral acid to give a compound of the formula:

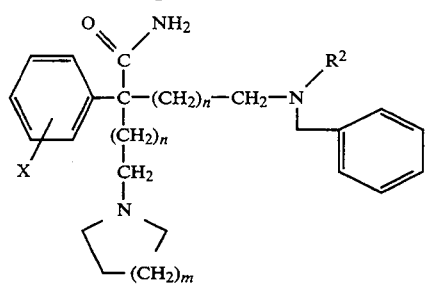

wherein R₂, X, m and n have the meaning defined above;

(e) debenzylating the product of step (d) using a supported palladium catalyst or a supported palladium (sulfited) catalyst with the proviso that when X is halo the supported palladium catalyst or the supported palladium (sulfited) catalyst is used in conjunction with a modifier to give a compound of the formula:

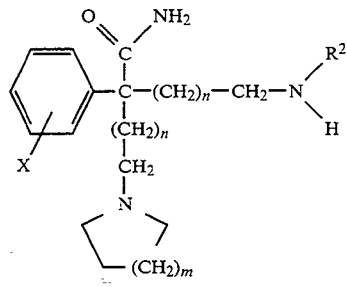

wherein R₂, X, m and n have the meaning defined above;

(f) acylating the product of step (e) using an anhydride having the following formula:

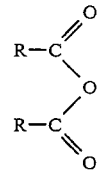

wherein R is methyl, phenyl, phenylmethyl or trifluoromethyl to give the compound of formula I wherein R₃ represents acetyl, benzoyl, phenacetyl or trifluoroacetyl, R² represents alkyl having 1 to 6 carbon atoms, X represents halo, alkyl having 1 to 6 carbon atoms, hydrido, trifluoromethyl, phenyl, or lower alkoxy having 1 to 6 carbon atoms.

2. A process according to claim 1 for preparing the compound of the formula

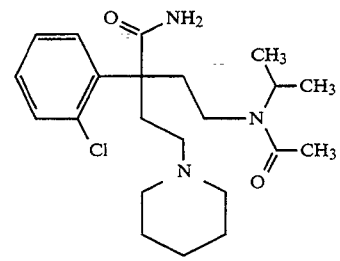

which comprises:
(a) alkylating 2-aminoethanol using benzaldehyde and ethanol in the presence of a platinum catalyst and hydrogen followed by reductive alkylation using acetone in the presence of a platinum catalyst and hydrogen to give 2-[(1-methylethyl)(phenylmethyl) amino]ethanol;
(b) halogenating 2-[(1-methylethyl) (phenylmethyl) amino]ethanol using a halogenating agent in the presence of an aprotic solvent to give N-(2-chloroethyl) -N-(1-methylethyl)benzenemethanamine, monohydrochloride;
(c) alkylating α-(2-chlorophenyl)-1-piperidinebutanenitrile with N-(2-chloroethyl)-N-(1-methylethyl)benzenemethanamine, monohydrochloride in the presence of base and dimethyl sulfoxide to give α-(2-chlorophenyl)-α-[2-[(1-methylethyl) (phenylmethyl)amino]ethyl]-1-piperidine butanenitrile;
(d) hydrating α-(2-chlorophenyl)-α-[2-[(1-methylethyl) (phenylmethyl)amino]ethyl]-1- piperidinebutanenitrile in the presence of mineral acid to give α-(2-chlorophenyl)-α-[2-[(1-methylethyl) (phenylmethyl)amino]ethyl]-1-piperidinebutanamide;

(e) debenzylating α-(2-chlorophenyl)-α-[2-[(1-methylethyl) (phenylmethyl)amino]ethyl]-1-piperidinebutanamide using a supported palladium catalyst or a supported palladium (sulfited) catalyst in presence of a modifier to give α-(2-chlorophenyl)-α-[2-[(1-methylethyl)amino]ethyl]-1-piperidine-butanamide; and (f) acetylating α-(2-chlorophenyl)-α-[2-[(1-methylethyl)amino]ethyl]-1-piperidinebutanamide in the presence of acetic anhydride to give α-[2-[acetyl (1-methylethyl)amino]ethyl]-α-(2-chlorophenyl)-1-piperidinebutanamide.

3. A process according to claim 2 wherein the halogenating agent is thionyl chloride.

4. A process according to claim 2 wherein the aprotic solvent is toluene.

5. A process according to claim 2 wherein the base is potassium hydroxide.

6. A process according to claim 2 wherein the mineral acid is sulfuric acid.

7. A process according to claim 1 for preparing an alkyl substituted phenylmethylaminoalkanol which comprises:

alkylation of an aminoalkanol using benzaldehyde or substituted benzaldehyde in the presence of an alkanol solvent, platinum catalyst and hydrogen at temperatures from 0° to 100° C. to give a phenylmethylamino alkanol and reductive alkylation of the said phenylmethylaminoalkanol using a dialkyl ketone in the presence of a platinum catalyst and hydrogen at temperatures from 0° to 100° C. to give an alkyl substituted phenylmethyl aminoalkanol.

8. A process according to claim 7 wherein the alkyl substituted phenylmethylaminoalkanol is 2-[(1-methylethyl) (phenylmethyl)amino]ethanol.

9. A process according to claim 7 wherein the aminoalkanol is 2-aminoethanol.

10. A process according to claim 1 for preparing a compound of the formula

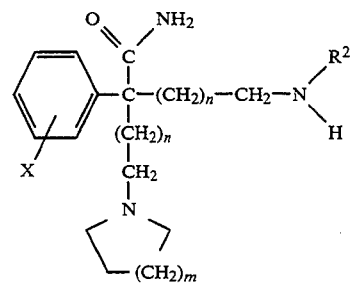

wherein X is halo, $R^2$ is alkyl having 1 to 6 carbon atoms, m is the integer 1 or 2 and n is an integer from 1 to 3 which comprises debenzylating a compound of the formula

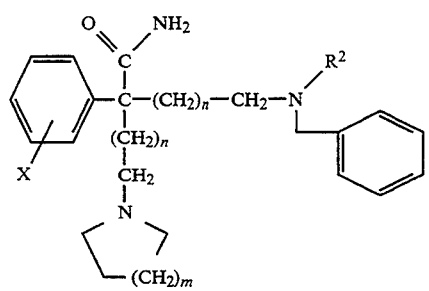

wherein X, $R^2$, m and n have the meaning defined above using a supported palladium catalyst or a supported palladium (sulfited) catalyst in the presence of a modifier at temperatures from 0° to 100° C. and hydrogen pressures from 0 to 100 psig.

11. A process according to claim 10 wherein the compound which is prepared is α-[2-[acetyl(1-methylethyl)amino]ethyl]-α-(2-chlorophenyl)-1-piperidinebutanamide.

12. A process according to claim 10 wherein the modifier is phosphorous acid.

13. A process according to claim 10 wherein the supported palladium catalyst is 5% palladium-on-carbon.

14. A process according to claim 10 wherein the supported palladium (sulfited) catalyst is 5% palladium-on-carbon (sulfited).

* * * * *